United States Patent [19]

Conti et al.

[11]  4,344,035
[45]  Aug. 10, 1982

[54] METHOD AND APPARATUS FOR DETERMINATION OF CHANGES IN THE SURFACE CHARGE OF MATERIALS

[75] Inventors: James C. Conti, East Northport; Eugene Findl, Amityville; William Wang, Forest Hills, all of N.Y.

[73] Assignee: BioResearch Inc., Farmingdale, N.Y.

[21] Appl. No.: 205,188

[22] Filed: Nov. 10, 1980

[51] Int. Cl.³ .............................................. G01N 27/00
[52] U.S. Cl. .................................................. 324/453
[58] Field of Search ............... 324/438, 452, 453, 459, 324/464, 466

[56] References Cited

U.S. PATENT DOCUMENTS 4,254,377  3/1981  Findl ................................... 324/453

*Primary Examiner*—Michael J. Tokar
*Attorney, Agent, or Firm*—Larson and Taylor

[57] ABSTRACT

A method and apparatus are disclosed for sensing the changes in the electrical potential across a double layer. By using a conductive plug comprised of the same material that are in suspension in a fluid, the present method can be used to determine the timing and amount of agents to be added to the liquid to promote the removal of the particle. In one embodiment, the sensor is comprised of two closed chambers, a sensor chamber closed by a porous plug made from the subject material, and a reference chamber closed by a plug that prevents particle dispersion therethrough and also offers a negligible variation in double layer interface potential. An exemplary plug could be comprised of agar. Each chamber includes a corresponding electrode probe and is filled with a conductive solution.

4 Claims, 10 Drawing Figures

METHOD AND APPARATUS FOR DETERMINATION OF CHANGES IN THE SURFACE CHARGE OF MATERIALS

FIELD OF THE INVENTION

The present invention relates to the sensing and measuring of changes in the electrical potentials formed at the boundary between a double-layer forming fluid and a solid caused by variations in the bulk electrolyte composition of the fluid. More particularly, in one preferred embodiment, the present invention relates to a method and apparatus for sensing the change in electrical potential across a double layer formed at the surface of a solid contacted by a liquid caused by additions or deletions of ions to the bulk liquid. The present invention also relates to the use of such an apparatus.

BACKGROUND OF THE INVENTION

The double layer concept was first described by Helmholtz in the last half of the nineteenth century and has been modified by many other since. In essence, an electrical double layer occurs at any phase boundary and consists generally of an immobile layer of ions next to the surface of one phase and a mobile layer of ions electrostatically in equilibrium with the ions in the immobile layer. Excellent reviews of double layer phenomena can be found in Smoluchowski, *Handbuch Der Elektrizitat und des Magnetismns,* Volume II, pp. 336-348, Lograetz, Editor, Leipsig, Barth, 1921 and Boumans, Physica 23, 1007-1026 (1957).

Furthermore, a more general description of the double layer can be found in two related patent applications by a different inventive entity, but including one of the present inventors. These applications, incorporated herein by reference in their entirety, are Findl et al Ser. No. 64,600 filed Aug. 7, 1979, now U.S. Pat. No. 4,254,377, and Findl et al Ser. No. 64,601 filed Aug. 7, 1979, now U.S. Pat. No. 4,274,937.

The discoveries that were reported in the above patent applications were made during some basic research programs. Further research was done in this area in response to the need for on-line process monitoring and optimization that exists in industry. More particularly, as supplies of high grade ores diminish, a greater emphasis will be placed on a process for mineral enrichment. In light of this, it is surprising to find that little on-line equipment exists.

The theory of the double layer has practical application whenever it is desired to measure changes in the surface charge of a solid in suspension in a liquid. One theory is that the solid can be taken out of suspension whenever the surface electrical properties at the solid liquid interface is favorable. Those processes are believed to include water purification, decantation, flocculation, centrifugation, calrification, thickening, froth floatation using microbubbles, electrofloatation, ultrafiltration, microfiltration, expression, electrophoresis, electrodialysis, electrodecantation, and electrochromatography. As a specific example, various floatation processes are commonly used throughout the country to upgrade low quality iron ores before smelting. However, as mentioned above, no on-line monitoring process is presently feasible so that the surface charge environment can be kept at an optimum state.

All known present on-line monitoring methods are slow, complex and are essentially batch approaches. There is, therefore, a need in the industry for a real-time, continuous measure of changes in the surface charge using a simple, inexpensive, accurate and compact sensor and using a simple method.

The prior art also contains numerous sensors which, with modification, could be used to measure effects on the double layer. However, presently available potentiometric electrochemical sensors, be they wire electrodes, ion specific electrodes, isfets or enzyme electrodes, are all used in conjunction with reference electrodes that present an interface of the test solution. Thus, these conventional electrodes are subject to signal interpretation errors, or interfaces that make them unsuitable for surface charge measurement.

SUMMARY OF THE INVENTION

The present invention provides a measurement of changes in the surface charge of materials as a function of changes in the ionic environment surrounding them. The present invention is based upon the measurement of an aspect of the electrochemical double layer that surrounds the solid when immersed in an ioncontaining fluid. This is a measurement of the change in the double layer potential caused by modifications of the ionic environment of that double layer. This effect has been designated as the change in the transbarrier potential.

According to one embodiment of the present invention, a sensor includes a porous active surface that is comprised of the material whose double layer properties are of interest, a first electrode probe on one side of the surface and out of physical contact with the liquid in which the sensor is to be immersed and a second electrode probe that is in effective physical contact with the liquid, but is mounted with or behind a means so as not to present an interface to the liquid which is immediately effected by a change of the ions in the liquid.

A method in accordance with the present invention for detecting variations in the electrolytic composition of a liquid comprises placing a porous solid material in the liquid whereby a double layer is formed between the material and the bulk of the fluid. A first passive sensor electrode is placed in electrical communication with one side of the material and thus on one side of the formed double layer. A second passive reference electrode is placed in electrical communication with the bulk of the fluid on the other side of the double layer, but is placed so that it does not present an interface to the liquid that is immediately affected by a change in the ions in the test solution.

Other features and advantages of the present invention are stated in or apparent from the detailed description of preferred embodiments found hereinbelow.

DETAILED DESCRIPTION OF THE PREFERRED EMBODIMENTS

Figure 1:
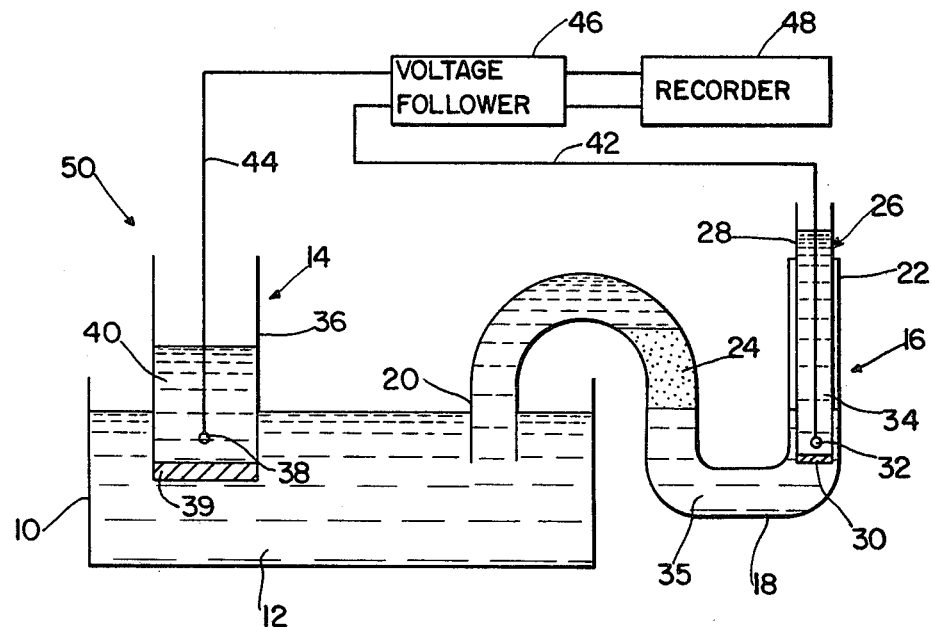
FIG. 1 is a diagrammatic representation of a sensor according to the present invention.

With respect to the figures in which like numerals indicate like elements throughout the several views, and in particular with reference to FIG. 1, there is a schematic depiction of a test apparatus that can be used to determine and explain the transbarrier potential.

A container 10 holds an ionic liquid 12 into which a sensor electrode 14 and a reference electrode 16 are immersed. Reference electrode 16 is comprised of an S-shaped tube 18 having one end 20 immersed in liquid 12 and the other end 22 open to the atmosphere. A cellulose polymer plug 24 is located in tube 18 effecting a blockage thereof while still permitting pressure equalization and ionic transport therein. Extending through open tube end 22 is an electrode chamber 26 comprised of a housing 28, a porous Vycor tip 30, and a silver-silver chloride electrode probe 32. Housing 28 is filled with an electrolytic solution 34 such as 20 kilo-ohm centimeter potassium chloride. A similar electrolytic solution 35 fills tube 18 between polymer plug 24 and open end 22. Liquid 12 fills the other end of tube 18 from end 20 to polymer plug 24.

Sensor electrode 14 is comprised of a housing 36 and an electrode probe 38, within housing 36. Electrode plug 38 can be, though it need not be, the same as electrode probe 32. A porous plug 39 is located in the end of housing 14. Porous plug 39 is made in known conventional ways of the material whose surface change is being investigated. For example, if the surface charge of sand is being monitored during the cationic floatation from non-magnetic ore then a porous silica plug, such as Vycor, can be used. Porous plug 39 is only porous to ionic transport or flow and not to liquid transport or flow. Almost any plug material can be made ionically porous, which means that it contains micropores that are defined as having a diameter of less than 0.001 inch. Other porous materials include filter cakes, foams, emulsions, and sintered metals.

Housing 36 is filled with an electrolytic solution 40 that can be the same as electrolytic solutions 34 and 35 in reference electrode 16.

Conductors 42 and 44 respectively connect electrode plugs 32 and 38 to the input of a high impedance voltage follower 46. Voltage follower 46 can be a commercially obtainable device with an exemplary input impedance of $10^{14}$ ohms. The output of voltage follower 46 is connected to the input of a recorder 48. Recorder 48 can be a commercially available device such as a Houston Omniscribe recorder.

It should be realized that sensor electrode 14 and reference electrode 16 together comprise a surface charge sensor, denoted 50. Obviously, FIG. 1 is merely a functional schematic diagram of a surface charge sensor 50 according to the present invention. However, a similar setup, but without incorporating a polymer plug 24 has successfully been used in laboratory experiments. In such a setup, the distant mounting of electrode plug 32 from tube end 20 provides an effective means for preventing ionic changes in liquid 12 from affecting reference electrode 16 for short time period testing. The amount of time that this type of arrangement can be used depends upon the diffusion of the ionic charges through tube 18 from liquid 12 to electrode plug 32. On the other hand, cellulose polymer plug 24 is a second means for keeping ionic changes occurring in liquid 12 from affecting reference electrode 16. Polymer plug 24 presents a barrier that exhibits low adsorptivity for ions used to modify the surface charge of a mineral or other solid in suspension in liquid 12. Other means include gels and polymers, such as agar, and, at least for certain ions, a Teflon film. Such a Teflon film that has been used has a thickness of from one-half to one thousandth of an inch and is obtained from Yellow Springs Instruments of Ohio.

Electrodes 14 and 16 are "passive" in that no external voltage is applied to either and they are used only to sense the electrical potential developed across a double layer. Furthermore, no chemical reaction is involved in their operation.

Although sensor 50 is depicted in FIG. 1 in only a schematic way, it does demonstrate that changes in the interfacial voltage between the active surface at the bottom of porous plug 39 and the bulk solution of liquid 12 can be measured. This can be more fully understood by considering the following example where sensor 50 is initially immersed in a 0.1 M NaCl solution. The initial voltage output of sensor 50 to voltage follower 47 will be the sum of all voltage drops occurring within it. Beginning with reference electrode 16, this summation includes:

| | | |
|---|---|---|
| 1. | The half cell potential of the silver-silver chloride electrode probe 32 | $E_1$ |
| 2. | The interfacial voltage across the double layer formed between the 20KΩcmKCl of solution 34 amd Vycor tip 30 | $E_2$ |
| 3. | The interfacial voltage across the double layer formed between Vycor tip 30 and the 20KΩcmKCl solution 35 | $E_3$ |
| 4. | The interfacial voltage across the double layer formed between solution 35 and the cellulose polymer plug 24 | $E_4$ |
| 5. | The interfacial voltage across the double layer formed between cellulose polymer plug 24 and liquid 12, the testing solution | $E_5$ |

The summation continues through the sensor electrode 14 as follows:

| | | |
|---|---|---|
| 6. | The interfacial voltage across the double layer formed between liquid 12 and porous plug 39 | $E_6$ |
| 7. | The interfacial voltage across the double layer between porous plug 39 and the 20KΩcm electrolytic solution 40 | $E_7$ |
| 8. | Half cell potential of the silver-silver chloride electrode probe 38 | $E_8$ |

Thus, the initial sensor voltage output, $E_I$, can be determined by the following equation:

$$E_I = E_1 + E_2 + E_3 + E_4 + E_5 + E_6 + E_7 + E_8 \tag{1}$$

Surface charge sensor 50 is constructed such that a change in the constituents of liquid 12 affects only interfacial voltages $E_5$ and $E_6$. The chemical and physical characteristics of cellulose polymer plug 24 are chosen such that interfacial voltages and any changes in them are small enough to be ignored. Alternatively, these interfacial voltages, $E_4$ and $E_5$ together with interfacial voltages $E_3$ and $E_4$ can be eliminated by removing polymer plug 24 and filling tube 18 with liquid 12. Obviously, although this slightly improves the accuracy of the results, such a sensor can only be used for a short period of time before the natural dispersion of the changed ionic additives to liquid 12 reaches Vycor tip 30. However, in a laboratory experiment, such a reference electrode was effective for at least the first five minutes after the ionic change to liquid 12.

A perturbation of liquid 12 with some component that affects the surface electrical properties of porous plug 39 will result in a change in the magnitude of $E_6$. This effect can now be noted as a change in the magnitude of the output voltage of sensor 50 to voltage follower 47. This can be mathematically written as follows:

$$E_F = E_1 + E_2 + E_3 + E_4 + E'_5 + E'_6 + E_7 + E_8 \quad (2)$$

Since $E_5$ approximately equals $E'_5$, substracting $E_I$ from $E_F$ results in the following:

$$E_F - E_I = E'_6 - E_6 \quad (3)$$

Thus, the change in interfacial voltage of porous plug 39, made from the material being investigated, reduces to the following equation:

$$\Delta E = \Delta E_6 \quad (4)$$

Because all of the other contributing interfacial voltages across the various double layers in sensor 50 are held constant, it can be seen that sensor 50 can be used to measure $\Delta E$, the interfacial voltage across across the double layer between porous plug 39 and liquid 12. Therefore, a sensor according to the present invention provides the ability to measure changes in the total double layer of any solid material that can be made ionically or electronically conductive. It should further be realized that although liquid 12 is described as an "ionic" liquid, depending upon the sensitivity of voltage follower 46 and recorder 47 together with the ability to reduce outside noise and interference, almost any liquid including some of which are thought to be insulators can be used.

A sensor and a method according to the present invention can also be used, for example, in water purification. In this embodiment, porous plug 39 is made from the contaminants to be removed, such as dirt. A Teflon film around the tip of tube 18 is used to replace polymer plug 24. Such a sensor has successfully been used to monitor the addition of surfactants to the water to control the surface charge therein so that the contaminating dirt can be flocculated.

Figure 4:
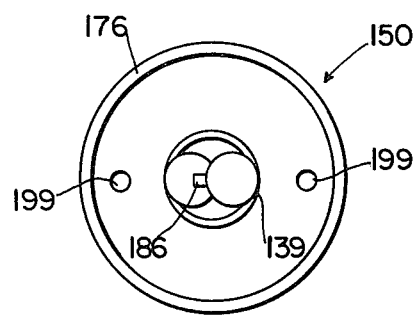
FIG. 4 is a bottom plan view of the sensor depicted in FIG. 3.

An experimental verification of the operation of a sensor similar to that depicted in FIG. 4 of the Findl et al applications was conducted in a floatation test apparatus. This apparatus is shown herein in FIG. 2.

Figure 2:
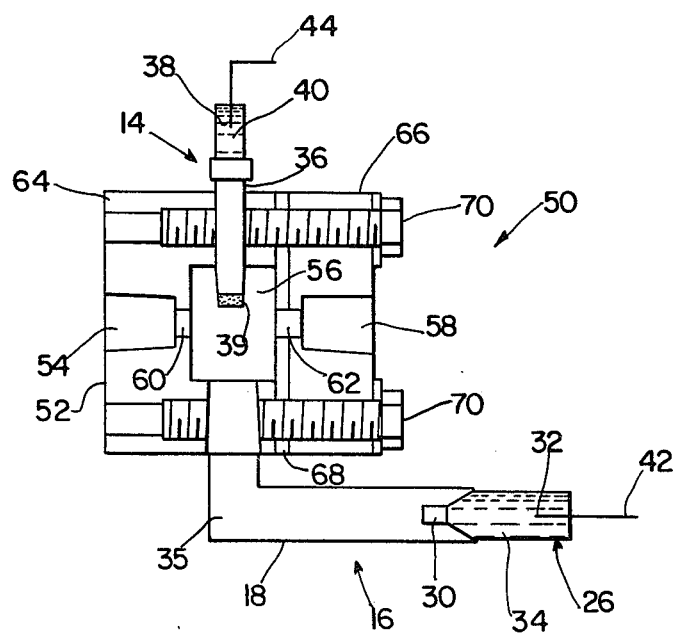
FIG. 2 is a side elevational view in cross-section of an embodiment of a sensor that is used to practice the present invention.

Sensor 50 shown in FIG. 2 includes most of the components of the sensor 50 depicted in FIG. 1 and therefore the same numbers are used. In addition, sensor 50 includes a housing 52 having an inlet port 54, a central chamber 56, and an outlet port 58. Two bores, 60 and 62, respectively connect inlet port 54 with chamber 56 and chamber 56 with outlet port 58. Thus, sensor 50 depicted in FIG. 4 is an on-line sensor that provides a flow path completely therethrough consisting of inlet port 54, bore 60, chamber 56, bore 62, and outlet port 58.

Housing 52 is preferably made of Delrin or Nylon in a first half 64 and a second half 66. A silicone rubber gasket 68 is used to form a liquid tight seal between housing halfs 64 and 66, which are held together with four bolts 70 (only two of which are shown).

An appropriate experimental, floatation test apparatus was used to obtain the pertinent data depicted in FIGS. 6-9. A floatation cell manufactured by Wemco Laboratory was connected with piping to a sensor 50, such as that depicted in FIG. 2. Other piping connected a Teel high solids pump and an air driven control valve to direct flow into the sensor or into a by-pass loop. The pump as driven by an electrically isolated, one-half horse power motor through an electrically insulating coupler on the connecting shaft. The test apparatus is believed to be sufficiently conventional as to be adequately described from the foregoing and therefore is not depicted.

Figure 5:
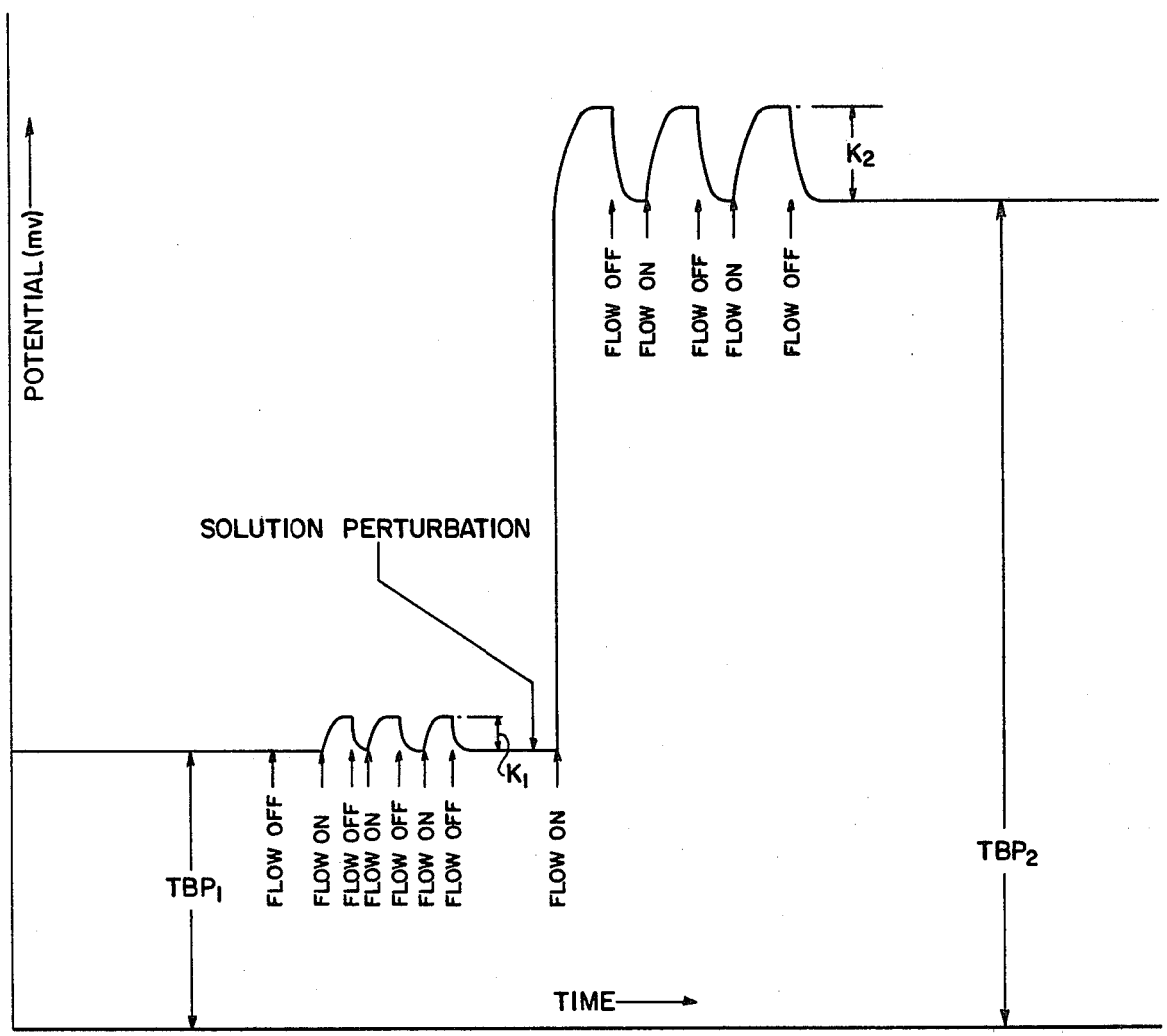
FIG. 5 is a diagrammatic graph of measured voltage signals over a period of time in which the relationship between the changes in the K-effect potential is depicted with respect to the changes in the transbarrier potential.
Figure 6:
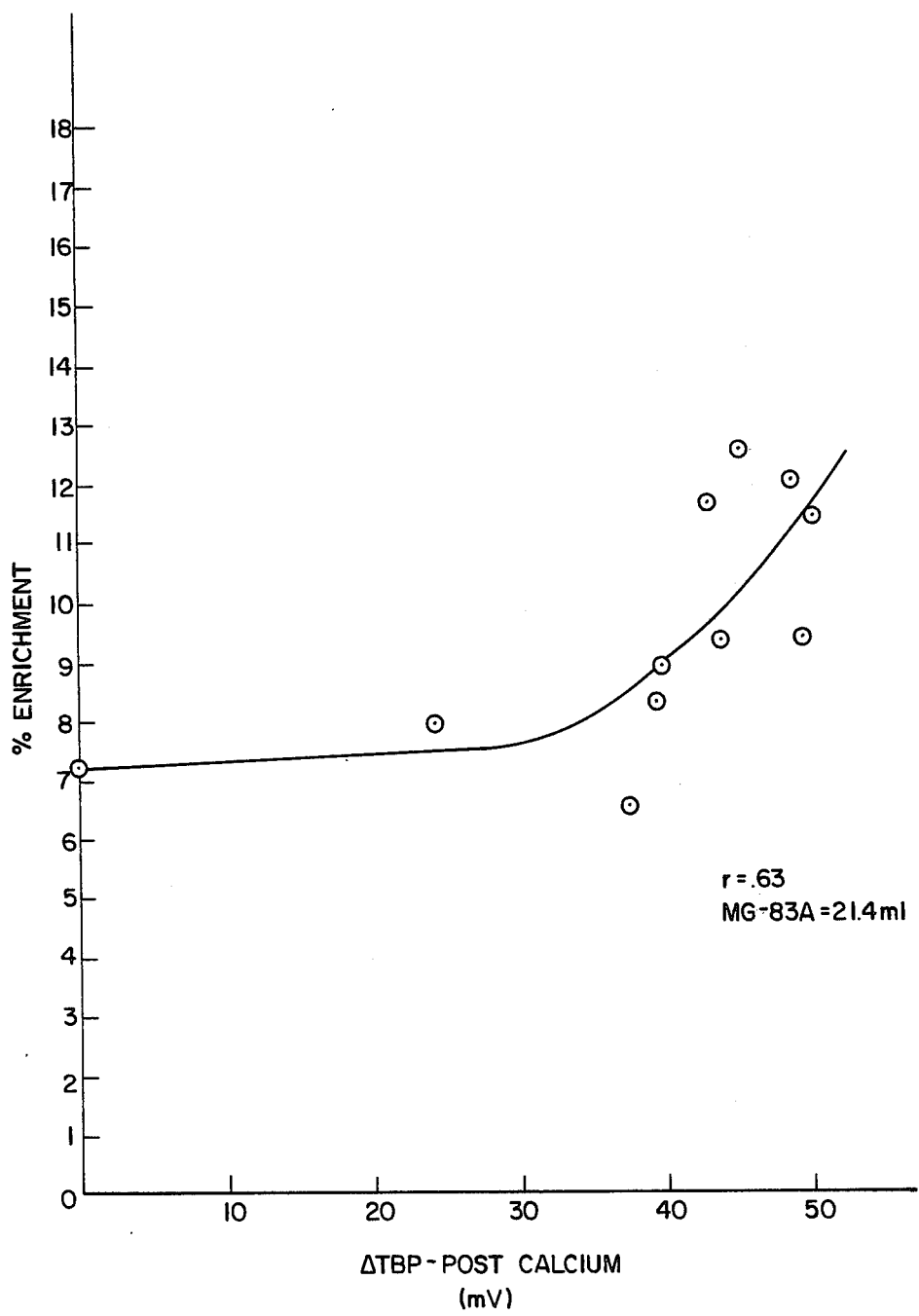
FIGS. 6–9 are the plotted graphs of the results from some experimentations.

With no flow by the sensor in the system, a surface modification agent was introduced and the valve was operated to direct the flow into the sensor. A K-effect signal and a reference transbarrier potential were measured both before and after the introduction of the agent. This result is diagrammatically shown in FIG. 5. The K-effect potential is described in the aforementioned Findl et al patent applications. The K-effect signal before agent introduction ($K_1$) and after ($K_2$) are depicted as changes in the initial transbarrier potential ($TBP_1$) and the final transbarrier potential ($TBP_2$), respectively. Not only is the final transbarrier potential greater than the initial transbarrier potential in FIG. 5, but also the final K-effect signal is greater than the initial one. These changes coincide with the expected changes in the zeta potential, that is, increased zeta potential results in increased K-effect signal.

The following experimental procedure was used and reference should be made to appropriate FIG. 6 through FIG. 9. However, the measured K-effect data is not included, the graphs only showing the measured transbarrier potentials.

A. Grinding and Flocculation

During the storage of ore samples, the surface characteristics of each individual particle change appreciably. In order to insure that a fresh surface is exposed during floatation, each batch was ground immediately before it was enriched. The following procedure was utilized in each case.

Grinding Procedure

1. Place 800 g ore into grinding mill.
2. Add 800 ml $H_2O$.
3. Grind for 3 minutes.
4. Wash all ore from mill into 4 liter beaker for flocculation step.

Flocculation is necessary to remove ultra small particles that interfere with the floatation process.

Flocculation Procedure

1. Fill beaker containing solids from grinding step with 3 liters $H_2O$.
2. Mix well.
3. Add flocculant.
4. Mix well for 1 minute.
5. Allow floc and solids to settle. Siphon liquid containing disposed fines.
6. Add flocculated solids to floatation cell.

B. Floatation Procedure

The following is an outline of the floatation procedure that was utilized indicating the points where various measurements were made. All runs began with 500,000 Ωcm water in an attempt to eliminate variations that might have occurred if tap water had been used.
1. Adjust pH of 4 liters water to 8.0 with NaOH.
2. Prepare starch solution (prepared fresh daily).
3. Floatation procedure
   Grind 800 g ore for 3 minutes.
   Flocculation of ore sample.
   Transfer ore to floatation cell (1200 rpm).
   Dilute to required level with pH=8 $H_2O$.
   Measure resistivity, TBP and K-effect, record pH.
   Add $CaCl_2$, 1.0 lb/LT ore.
   Measure resistivity, TBP and K-effect.
   Add starch, 0.5 lb/LT ore.
   Measure resistivity, TBP and K-effect.
   Adjust pH with $H_2SO_4$ or NaOH.
   Measure resistivity, TBP and K-effect.
   Adjust resistivity to fit final level using NaCl (5,000 Ωcm).
   Measure resistivity, TBP and K-effect.
   Add MG-83A, 0.5 lb/LT.
   Measure resistivity, TBP and K-effect.
   Open air valve, collect for 5 minutes.
   Measure TBP and K-effect.
   Collect another 5 minutes.
   Final measurement, resistivity, pH, temperature, K-effect, and TBP.

C. Chemical Analysis

A chemical analysis was done on the ore before and after floatation in order to properly quantitate results. A titrimetric procedure was used for an iron determination. The following analytical scheme was used:
1. Three samples each were taken of the original ore, enriched ore and material removed at floatation.
2. Samples were filtered and dried.
3. A 0.3 g sample was weighed, transferred to a flask and dissolved, via acid.
4. All $Fe^{+3}$ present was reduced to $Fe^{+2}$ via $Sn^{+2}$.
5. All $Fe^{+2}$ was then oxidized to $Fe^{+3}$ using $K_2Cr_2O_7$.
6. Equivalents of oxidizing agent=equivalents total iron.

D. Experimental Variables

There were three distinct series of experiments designed such that cross comparisons could be made between a set of conditions common to each group. In this way, system reproducibility was checked from series to series.

Calcium series—While holding all other experimental conditions constant (see B) $CaCl_2$ dosage was varied through 0.5, 0.75, 1.0 and 1.5 lb/LT. All conditions were run in triplicate.

MG-83A series—While holding all other experimental conditions constant (see B) MG-83A dosage was varied through 0.1, 0.3, 0.5 and 0.75 lb/LT. All conditions were run in triplicate.

pH series—While holding all other experimental conditions constant (see B) pH was varied through 8, 9 and 10. All conditions were run in triplicate.

Below is a listing of solution information:
MG-83A (0.5%) 2.5 g/500 ml.
$CaCl_2$ (1.0%) 5 g/500 ml.
NaOH (10%) 50 g/500 ml.
$H_2SO_4$ (1 M) 25 ml/500 ml.
Starch* (1.25%) 6.25 g/500 ml.
*Prepare starch solution daily.

E. Results

As indicated above, electrical measurements (both TBP and K-effect) were made after each of the seven steps that comprised the floatation process. Each set of conditions was run in triplicate and finally the pre- and post-floatation chemical analyses were done in triplicate for each individual run. Data were tabulated separately for each series since the extreme variation in $Ca^{+2}$ that was introduced does not reflect the conditions that might be met by the mining industry. TBP, K-effect and the change in both that accompanied each of the seven floatation steps were correlated with percent enrichment and volume of reagent utilized.

Fifty-one single and eight multivariable regressions were run. Best fits were obtained with the single variable analysis. Correlation coefficients are reported only for comparisons between voltage signals (or change thereof) and percent enrichment since these correlations were the most encouraging.

Correlation coefficients reported (and noted on the graphs) are for single variable (or straight line) correlations even though the lines (curves) drawn reflect the most realistic response. In addition all error bars indicate plus and minus the standard error of the mean (±SEM).

F. $CaCl_2$ Series

As noted above, the floatation conditions that were created in this series do not necessarily reflect ranges in $Ca^{+2}$ that any mining operation might experience.

Figure 7:
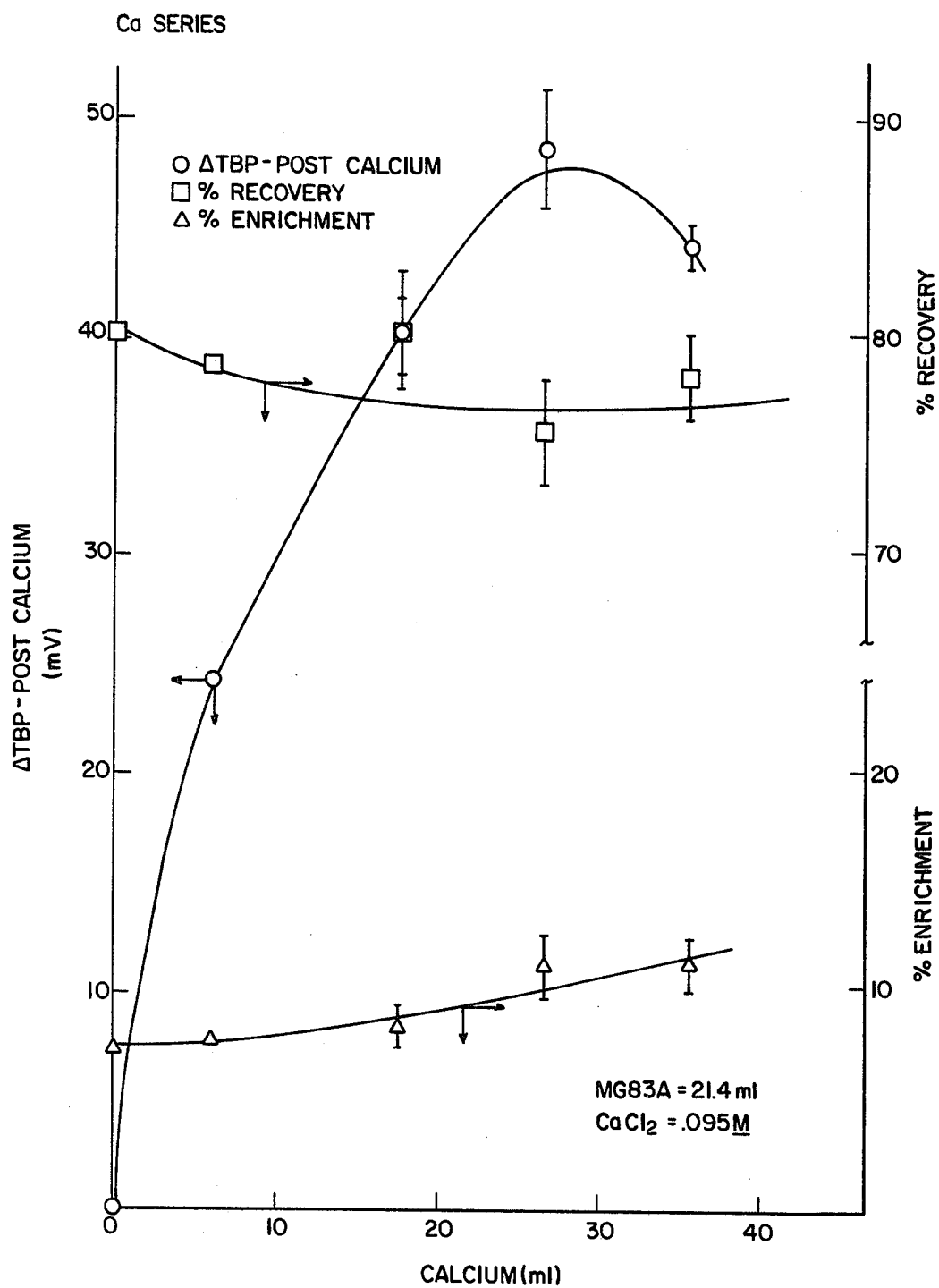

In this series, the best correlations that were obtained matched (1) percent enrichment versus the K-effect after MG-83A was added (K-effect post MG) (r=0.54), and (2) the change in the transbarrier potential that accompanied the addition of $CaCl_2$ (ΔTBP post calcium) (r=0.63). This ΔTBP post calcium can also be expressed as the TBP pre MG-83A. This data is plotted in FIG. 6. FIG. 7 is a composite of data reflecting how the ΔTBP post calcium percent enrichment and percent recovery (that percent of initial ore recovered in enriched form) vary with respect to volume of $CaCl_2$ solution added.

G. MG-83A Series

The Cleveland Cliffs floatation plant (an internationally recognized model operation) is set up in such a way that the fine tuning of floatation conditions, on a semicontinuous basis, is accomplished by varying the amount of collector that is added. For this reason the MG-83A collector concentration series presented in this section most closely approximates the kind of variation in floatation conditions that are encountered during the actual mining operation.

Figure 8:
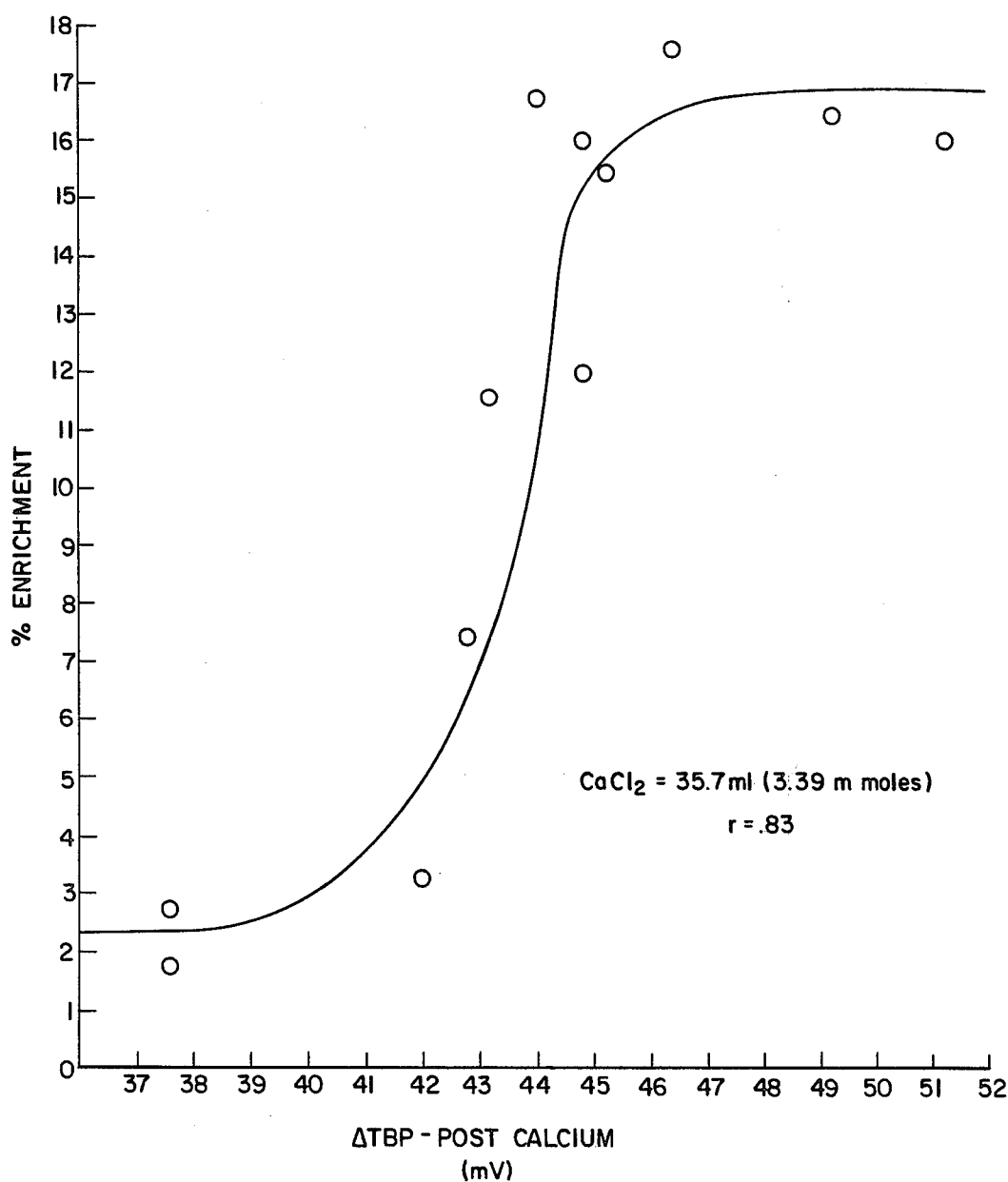
Figure 9:
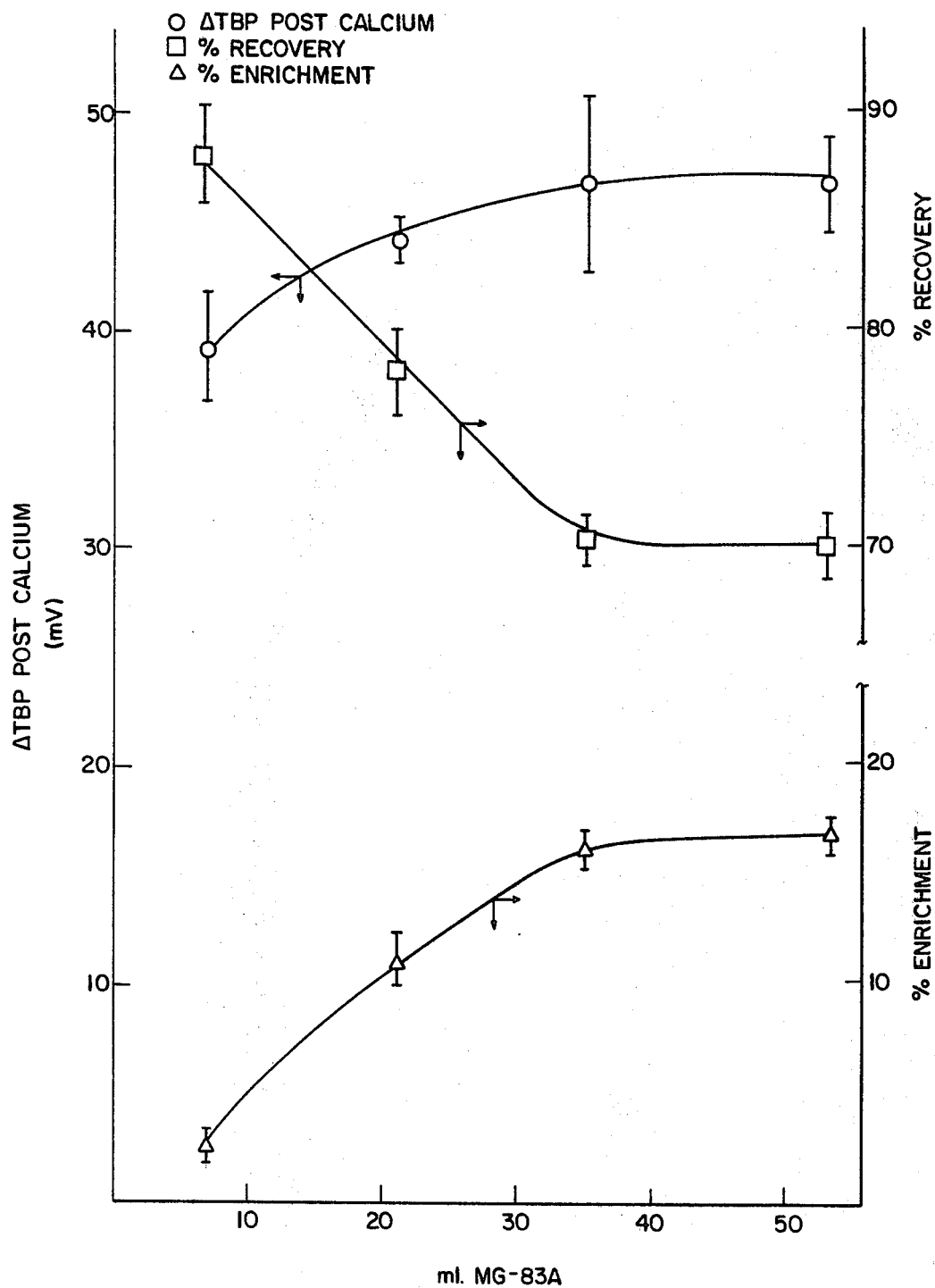

Initial measurements were made after the ore was added to the floatation cell. A usable correlation was found between percent enrichment and the ΔTBP associated with addition of calcium. This could also be expressed as the magnitude of the TBP just prior to collector addition. FIG. 8 is a plot of this data versus percent enrichment. The curve has the well known titration-like S-shape. Even with this shape, the correlation coefficient for a straight line is r=0.83. In FIG. 9 this ΔTBP data is plotted vs ml of MG-83A along with the corresponding percents enrichment and recovery.

The ΔTBP and % enrichment curves have very much the same shape. In addition, the ΔTBP data is on the order of 40–50 mV, a signal magnitude easily measured and not nearly as susceptible to noise artifacts as the smaller K-effect.

Collector addition, as mentioned above, is the point in the process where the mining industry makes fine tuning adjustments to the procedure. It was found that measurements associated with this step would result in data that could be used by the plant technicians to more effectively administer the collector. The ΔTBP post calcium and TBP pre MG-83A data were statistically most encouraging and at the same time were all associated with the collector addition.

H. pH Series

No results are shown for this series. Data was obtained as the pH was varied between 8 and 10. Based upon iron ore floatation data in the literature, changes in pH in the range noted should have no effect on the zeta potential of silica. The test data confirmed this information.

The above test results confirm that transbarrier potential measurements, just prior to and post addition of the collector, can be predictive of the resulting percent enrichment that an ore sampling is undergoing. The monitoring of this step is very important since it is this reagent that the mining industry generally varies on a continuous basis. The resulting transbarrier potential signals have a sufficiently large enough magnitude so as to be readily measurable and less affected by artifacts. Furthermore, the measurement of the transbarrier potential is not dependent upon a differential flow, necessary for the measurement of the K-effect, and in fact does not need any flow.

Figure 3:
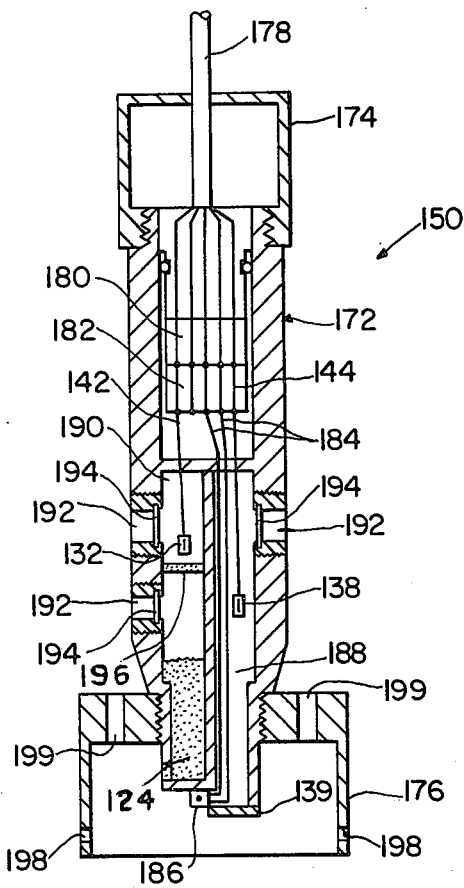
FIG. 3 is a side elevational view in cross-section of a second embodiment of the present invention.
Figure 10:
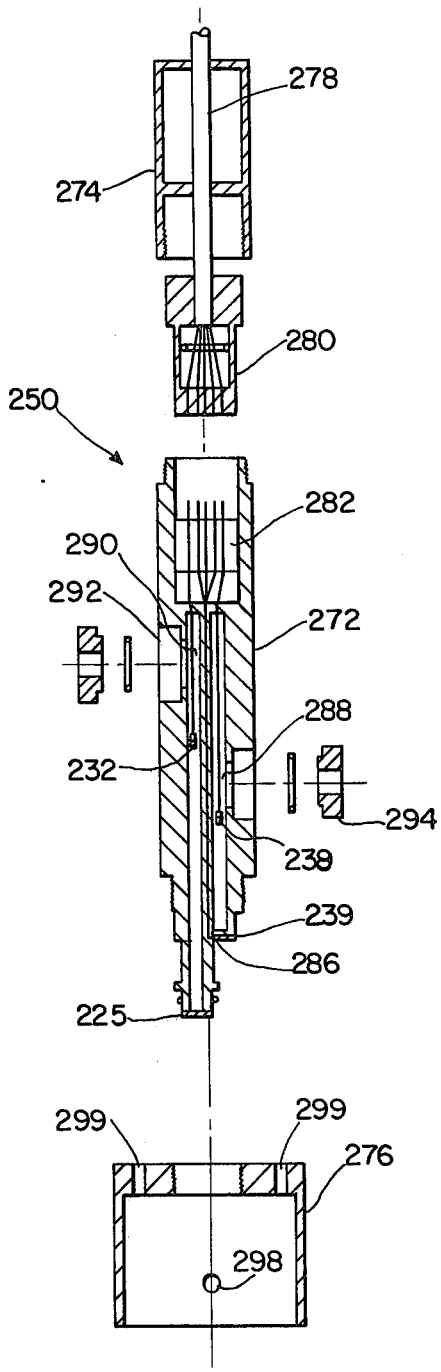
FIG. 10 is an exploded view in cross-section of a further embodiment of a sensor according to the present invention.

An alternate design of a sensor according to the present invention is depicted in FIGS. 3 and 4 and is denoted 150. A slightly modified version in a further embodiment of a sensor is depicted in FIG. 10 and is denoted 250. Elements which are in common with sensors 150 and 250 with sensor 50 depicted in FIG. 2 are denoted by using the same units and tens digits.

Surface charge sensor 150 is a portable, submersible-type sensor. Sensor 150 comprises a housing 152 that includes an elongate body 172, a fluid-tight, threaded cap 174 threaded onto one end of body 172, and a protective shield 176 threaded onto the other end of body 172. A multiwire cable 178 protrudes through a watertight fitting through cap 174 and terminates in a plug 180. A mating plug 182 mounted inside housing 152 permits easy electrical connection and disconnection. Conductor 142, connected to electroprobe 132 and conductor 144, connected to electrode probe 138, comprise two of the five wires. Two other conductors 184 are connected to a thermistor 186 to provide accurate temperature measurement of the fluid. The last conductor is for ground.

The lower end of elongate body 172 is divided into two chambers, a sensor chamber 188 and a reference chamber 190. Sensor chamber 188 corresponds to sensor housing 36 and reference chamber 192 corresponds to tube 18 of sensor 50. A sensor electrode probe 138 is mounted in sensor chamber 188 and a reference electrode probe 132 is mounted in reference chamber 190. Each one of chambers 188 and 190 also includes a fill port 192 that has a threaded cover or plug with a rubber diaphragm located at the interior end thereof so as to permit pressure variations within the corresponding chamber.

Reference chamber 190 also includes a second fill port 192 and cover 194 located below a porous silica barrier 196. Barrier 196 is to provide further isolation of electrode probe 132 from the ionic changes in the fluid to be measured. The lower fill port 192 is located below barrier 196 so that a plug 124 can be inserted therein. For sensor 150, a presently preferred plug 124 is comprised of agar which can be poured in as a fluid and then solidifies to a gelatin-like consistency. An access port 197 located in the lower end of reference chamber 190 provides access for ionic flow or transport from the liquid being investigated to reference electrode probe 132.

Sensor chamber 188 is preferably filled through port 192 with an electrolytic solution, such as a potassium chloride solution. Similarly, a potassium chloride solution fills reference chamber 190 on both sides of barrier 196.

Shield 176 has an open bottom and is provided with aligned orifices 198 in the lower portions of the side so as to permit fluid flow therethrough. Two vent holes 199 in the top of shield 176 permit sensor 150 to be easily inserted into a fluid.

With reference now also to FIG. 10, surface charge sensor 250 is similar to sensor 150 shown in FIG. 3 and FIG. 4. However, barrier 196 is omitted from reference chamber 290 and reference chamber 290 extends below sensor chamber 288, where the reverse is true in sensor 150. Finally, the other major differences are that reference chamber 290 has only one fill port 292 and plug 124 has been omitted and replaced with a thin Teflon film 225 completely covering the bottom opening of chamber 290.

As mentioned above, surface charge sensors 50, 150, and 250 respond to predicted changes in the fluid. When used for iron ore enrichment through conventional floatation processes, the sensors respond to predicted changes in the surface electrical properties of colloidal silica during the floatation process. When used to measure the transbarrier potential, a distinct measurement can be made that is a function of the ionic composition of the double layer on the silica provided that the porous plug 39, 139 or 239 is also made of silica. In particular, the sensor supplies data related to the percent enrichment that an ore sample undergoes as floatation reagents are added. The data depicted in the figures were obtained while monitoring the cationic floatation of silica from non-magnetic ore samples. A collector, which can be a long chain amine, is added to a slurry of the ore. Surface electrical characteristics of the silica result in specific adsorption of the amine. This renders the silica or quartz particles hydrophobic. If air bubbles are introduced to attract the hydrophobic particles, they can be carried to the surface for removal by conventional means. Pretreatment of the ore with surface modification agents renders the iron oxide particles less likely and the silica particles more likely to adsorb the amine. The addition of the agents can be controlled by monitoring the transbarrier potential changes measured with a method and sensor according to the present invention.

The following chart indicates the relative measurements of the K-effect potential and the transbarrier potential change.

| MEASUREMENT* | ADD ORE | CaCl₂ | STARCH | AMINE | % Fe INITIAL | % Fe FINAL | % ENRICHMENT | COMMENTS |
|---|---|---|---|---|---|---|---|---|
| | | | | | STEP → | | | |
| K-EFFECT | 4.8 | .6 | .74 | .70 | 47.5 | 55.54 | 8.04 | T = 36° C. |
| Δ TBP | 32 | 46.4 | −.16 | .56 | | | | pH = 7.8 |
| K-EFFECT | 4.08 | .85 | .62 | .64 | 46.33 | 58.41 | 12.08 | T = 34° C. |
| Δ TBP | 44 | 41.6 | −.34 | .34 | | | | pH = 8.0 |

*All data in millivolts

Although the invention has been described in detail with respect to exemplary embodiments, thereof, it will be understood by those of ordinary skill in the art that variations and modifications may be effected within the scope and spirit of the invention.

We claim:

1. A method for detecting variations in the electrolytic composition of a liquid comprising
    placing a conductive solid material in the liquid whereby a double layer is formed between the material and the bulk of the fluid;
    placing a first passive sensor electrode in electrical communication with one side of said material and hence on one side of the double layer;
    placing a second passive reference electrode in electrical communication with the bulk of the liquid on the other side of the double layer, but out of any contact with the liquid that would affect the double layer formed on said reference electrode at the same time there is an affect on the double layer formed on said solid material when the electrolytic composition of the liquid is changed;
    determining the electrical potential between said electrodes at a reference time to establish a reference potential between said electrodes; and
    comparing said reference potential with a later determined electrical potential and thereby obtaining the change to the transbarrier potential.

2. A method as claimed in claim 1 for use to determine the change in the surface charge of a known substance suspended in the liquid wherein said conductive material is made of said known substance.

3. A method as claimed in claims 1 or 2 and wherein said reference electrode includes an electrode probe and said method further includes providing a means for preventing a change in the electrolytic composition from immediately affecting said reference electrode plug between said reference electrode plug and the liquid.

4. A method for detecting the changes in the surface charge of a solid material in a liquid comprising
    placing a first, passive sensor electrode in contact with the liquid, said sensor electrode including
        a housing, a surface portion of which is comprised of a conductive substance of the same composition as said solid material;
        and said sensor having an electrode plug;
    placing a second, passive reference electrode in contact with the liquid, said reference electrode including;
        an electrode plug, and
        means for preventing a change in the electrolytic composition from immediately affecting said reference electrode plug;
    determining the electrical potential between said electrode plugs at a reference time to establish a reference potential;
    determining the electrical potential between said electrode plugs at a later time; and
    comparing said reference potential with said later determined potential so as to permit a determination of the change in the surface charge of said solid material.

* * * * *